US009701848B2

(12) United States Patent
Landau et al.

(10) Patent No.: US 9,701,848 B2
(45) Date of Patent: Jul. 11, 2017

(54) BIOACTIVE, RUTHENIUM-CONTAINING COATING AND DEVICE

(75) Inventors: Uwe Landau, Berlin (DE); Thomas Lisowsky, Monheim (DE); Karlheinz Esser, Moenchengladbach (DE); Klaus-Dieter Mehler, Muelheim an der Ruhr (DE)

(73) Assignee: AGXX INTELLECTUAL PROPERTY HOLDING GMBH, Berlin (DE)

( * ) Notice: Subject to any disclaimer, the term of this patent is extended or adjusted under 35 U.S.C. 154(b) by 1155 days.

(21) Appl. No.: 12/445,254

(22) PCT Filed: Oct. 2, 2007

(86) PCT No.: PCT/EP2007/008564
§ 371 (c)(1),
(2), (4) Date: Jan. 28, 2010

(87) PCT Pub. No.: WO2008/046513
PCT Pub. Date: Apr. 24, 2008

(65) Prior Publication Data
US 2010/0143431 A1 Jun. 10, 2010

(30) Foreign Application Priority Data
Oct. 13, 2006 (DE) .................. 10 2006 049 108

(51) Int. Cl.
*C09D 5/14* (2006.01)
*A01N 59/16* (2006.01)
*C02F 1/50* (2006.01)
*A61M 25/00* (2006.01)

(52) U.S. Cl.
CPC ............... *C09D 5/14* (2013.01); *A01N 59/16* (2013.01); *C02F 1/505* (2013.01); *A61M 2025/0056* (2013.01)

(58) Field of Classification Search
None
See application file for complete search history.

(56) References Cited

U.S. PATENT DOCUMENTS

| 4,863,510 | A | | 9/1989 | Tamemasa et al. | |
|---|---|---|---|---|---|
| 5,520,664 | A | * | 5/1996 | Bricault et al. | ........... 604/265 |
| 6,113,636 | A | * | 9/2000 | Ogle | ........... 623/11.11 |
| 6,716,895 | B1 | | 4/2004 | Terry | |
| 6,949,598 | B2 | | 9/2005 | Terry | |
| 2003/0049300 | A1 | | 3/2003 | Terry | |
| 2003/0068509 | A1 | * | 4/2003 | Shah et al. | ........... 428/472 |
| 2004/0167257 | A1 | * | 8/2004 | Ryang | ........... 524/262 |
| 2005/0037048 | A1 | * | 2/2005 | Song | ........... 424/423 |
| 2005/0170011 | A1 | | 8/2005 | Yanagihara et al. | |
| 2006/0154911 | A1 | | 7/2006 | Batarseh | |

FOREIGN PATENT DOCUMENTS

| JP | 7-188456 A | 7/1995 |
|---|---|---|
| JP | 2003-529630 A | 10/2003 |
| JP | 2005-296764 A | 10/2005 |
| JP | 2008-526873 A | 7/2008 |
| WO | 0046438 A1 | 8/2000 |
| WO | 0143788 A2 | 6/2001 |
| WO | 2004011672 A1 | 2/2004 |
| WO | 2004039735 A1 | 5/2004 |

OTHER PUBLICATIONS

Allardyce, Clair S. et al, Synthesis and characterization of some water soluble ruthenium(II)-arene complexes and an investigation of their antibiotic and antiviral properties, Journal of Organometallic Chemistry (2003), vol. 668, pp. 35-42.*
Pohl, Karsten, Stability of Nanostructures on Surface, Dekker Encyclopedia of Nanoscience and Nanotechnology (Mar. 31, 2004), pp. 3675-3683.*
Coen, M.C., et al., Modification of catheter materials by coating with polymer layers containing silver, Macromolecular Symposia (Jan. 1996), vol. 103, Issue 1, pp. 109-117.*
Merriam Webster, bound definition, accessed Nov. 17, 2014, pp. 1-5.*
Wu et al., "Characterization of Silica-Supported Cu Monometallic and Ru—Cu Bimetallic Catalysts by Hydrogen Chemisorption and NMR of Adsorbed Hydrogen," Journal of Catalysis, vol. 121, 1990, pp. 271-293.
Wu et al., "Characterization of Silica-Supported Ru—Ag and Ru—Au Bimetallic Catalysts by Hydrogen Chemisorption and NMR of Absorbed Hydrogen," Journal of Catalysis, vol. 123, 1990, pp. 43-59.
Schmidt et al., "PtRu Alloy Colloids as Precursors for Fuel Cell Catalysts," J. Electrochem. Soc., vol. 145, No. 3, Mar. 1998, pp. 925-931.
Blokhina et al., "Antioxidants, Oxidative Damage and Oxygen Deprivation Stress: a Review," Annals of Botany, vol. 91, 2003, pp. 179-194.
Elhafi et al., "Microwave or Autoclave Treatments Destroy the Infectivity of Infectious Bronchitis Virus and Avian Pneumovirus but Allow Detection by Reverse Transcriptase-Polymerase Chain Reaction," Avian Pathology, vol. 33, No. 3, Jun. 2004, pp. 303-306.

(Continued)

*Primary Examiner* — Dennis J Parad
*Assistant Examiner* — Lyndsey Beckhardt
(74) *Attorney, Agent, or Firm* — Joyce von Natzmer; Agris & von Natzmer, LLP

(57) ABSTRACT

The invention relates to the production and use of novel bioactive devices and metallic coatings for example for sterilizing, disinfecting, and decontaminating water or aqueous solutions. The known oligodynamic effect of silver for reducing the amount of germs is thereby improved and increased by combining silver with ruthenium and a vitamin or derivative thereof. The novel properties of these bioactive metal surfaces lead to faster and more efficient killing of microorganisms. Simultaneously, these novel bioactive metal surfaces prevent infestation by microorganisms and attachment or permanent deposition of problematic biomolecules such as for example DNA, RNA, or proteins. A self-cleaning surface is thus obtained, which very quickly and efficiently and over extended periods of time sterilizes water and aqueous solutions when they come in contact with said surface.

32 Claims, 6 Drawing Sheets

(56) References Cited

OTHER PUBLICATIONS

Veal et al., "The Influence of Reducing Agent and 1,10-Phenanthroline Concentration on DNA Cleavage by Phenanthroline + Copper," Nucleic Acids Research, Oxford University Press, vol. 19, No. 12, 1991, pp. 3383-3388.
Padayatty et al., "Vitamin C as an Antioxidant: Evaluation of Its Role in Disease Prevention," Journal of the American College of Nutrition, vol. 22, No. 1, 2003, pp. 18-35.
PCT International Preliminary Report on Patentability of International Application No. PCT/EP2007/008564 issued Jul. 7, 2009.

* cited by examiner

Fig. 2A-D
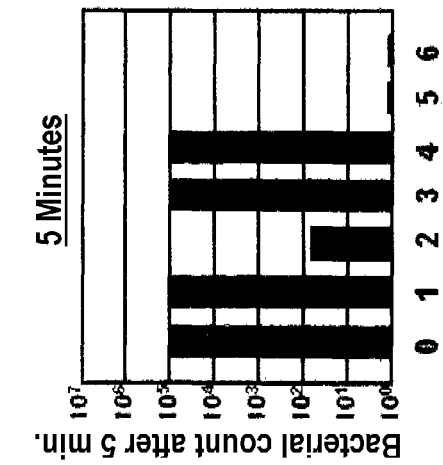
2A
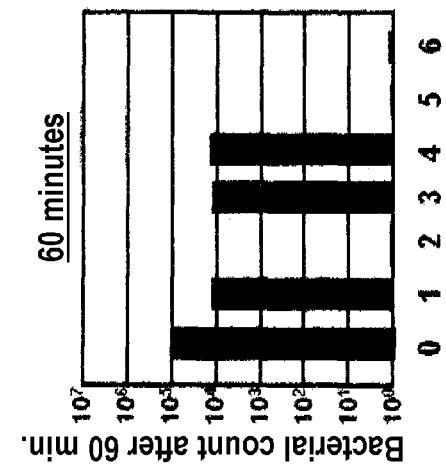
2B
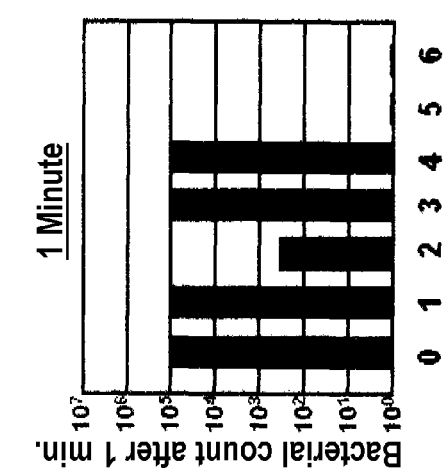
2C
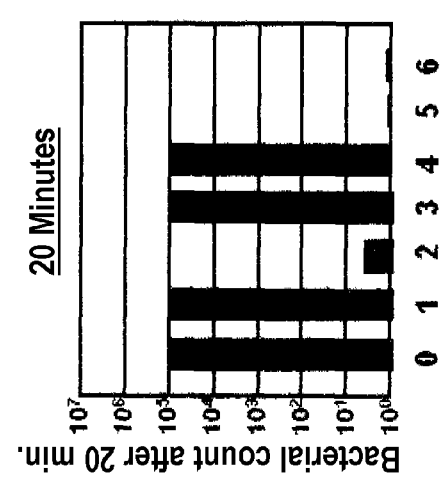
2D

Fig. 3A-D
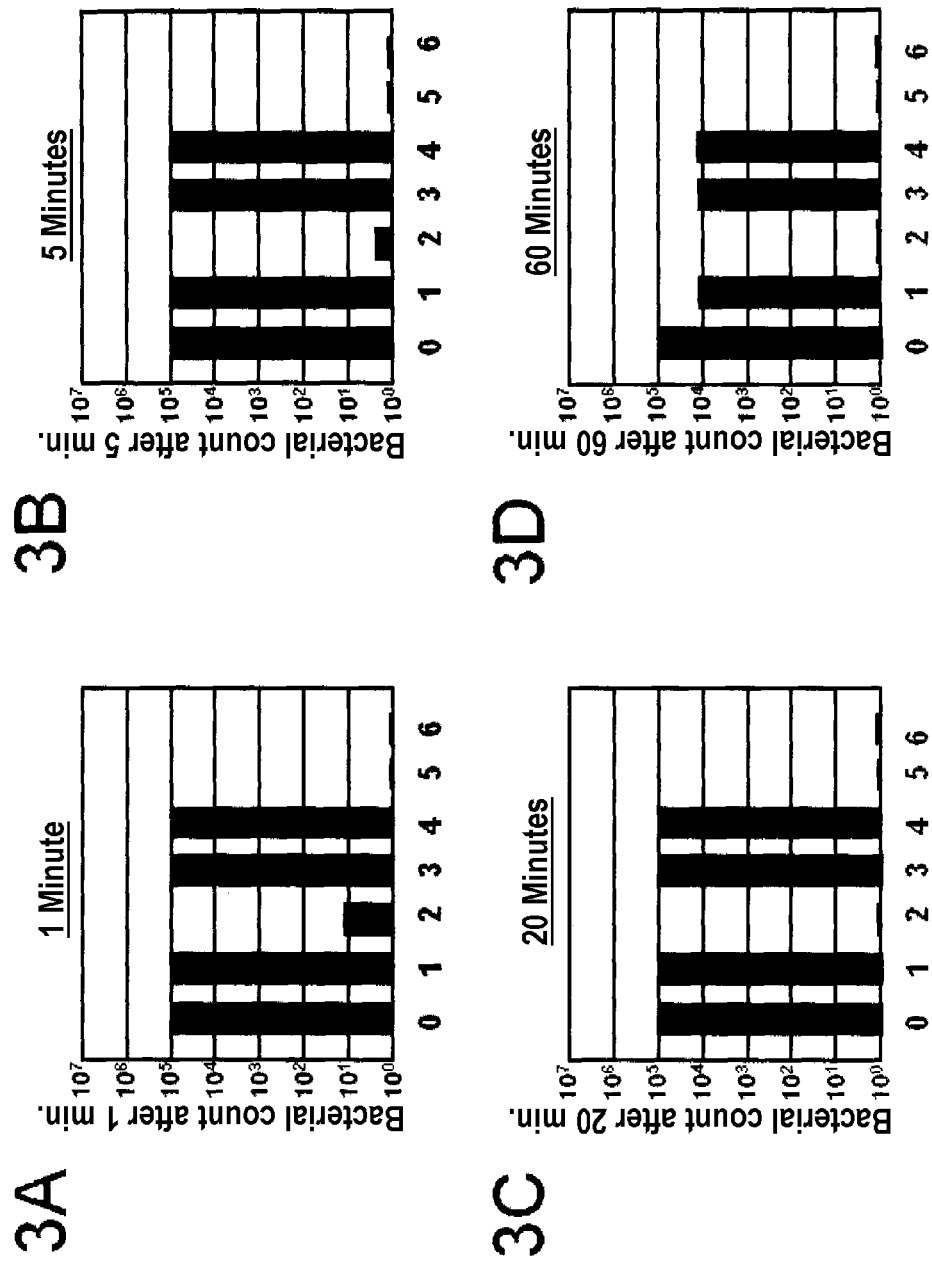

BIOACTIVE, RUTHENIUM-CONTAINING COATING AND DEVICE

This is the U.S. national stage of International application PCT/EP2007/008564, filed Oct. 2, 2007 designating the United States and claiming priority to German application DE 10 2006 049 108.4, filed Oct. 13, 2006.

BACKGROUND OF THE INVENTION

The present invention relates to a bioactive, ruthenium-containing coating, in particular for silver-containing surfaces, and a bioactive device having a silver- and ruthenium-containing surface, and the production and use of said bioactive coating and device.

As early as 1869 by Ravelin and 1893 by von Nägeli, the antibacterial effect of silver in very low doses was described. Even today, the effectiveness of silver is still of immediate interest (Landau, U. (2006): Die keimreduzie-rende Wirkung des Silbers in Hygiene, Medizin und Wasserauf-bereitung: Die Oligodynamie des Silbers; Isensee-Verlag, Oldenburg, 2006 Oct. 3).

Microbial contaminations continue to cause huge problems and commercial losses in all areas associated with water quality, aqueous solutions, and hygiene. Such areas can be found for example in hospitals, hygiene institutes, in food technology, production, air-conditioning technology, and also in the home.

For this reason, various antimicrobial decontamination solutions using aggressive chemical substances against microorganisms, such as for example formaldehyde, alcohols, phenols, sodium azide, sodium hypochlorite, or strongly oxidizing agents such as for example hypochlorite, bleaching agents, or mineral acid have existed for quite some time.

The disadvantages of these solutions and methods lie in the fact that the very aggressive chemicals and oxidizing agents used for decontamination and disinfection have a high corrosive and toxic potential. As a result, treated water and aqueous solutions typically become unsuitable for human consumption and used devices or surfaces can be damaged by corrosion.

Such aggressive chemical solutions for washing and rinsing devices, instruments, and working surfaces are therefore typically used in closed loops.

The application of silver technology gradually improved this problem. The oligodynamic effect of silver allows the sterilization of water or aqueous solutions in a quality that represents no health hazard to humans and prevents damage to materials and surfaces. Silver technology is therefore also used in the production, treatment, and quality assurance of drinking water.

Consequently, there is a constant effort to improve the efficiency of silver technology. For example, from WO 2005/023206 A2 and DE 100 54 248 A1 more recent methods are known that utilize the properties of nanoparticles to achieve a quicker release of silver ions over a very large surface.

The commercial interest in materials and methods for maintaining the water quality or the quality of aqueous solutions in general for humans by means of silver technology is emphasized by the widespread commercial distribution of corresponding products under various trade names.

Disadvantages of the known methods for silver technology are a strongly delayed onset of the action after contact of silver with water and only selective antibacterial action. It takes for example usually several hours, frequently even significantly longer, until a sufficient quantity of silver ions is released from the surface after contact of silver with contaminated water to sufficiently kill the microorganisms and achieve an adequate sterilization of the water.

Hence, silver technology has two problem areas: 1. time-delayed onset of the germicidal action; and 2. limited activity spectrum for efficient decontamination and disinfection of water or aqueous solutions to kill or eliminate microorganisms and problematic biomolecules. Improved methods and processes are therefore constantly sought to increase the efficiency of silver technology.

Furthermore, the new findings of modern molecular biology and gene technology show that besides microorganisms, genetic information alone, individual genes or even parts thereof, and certain proteins are already sufficient to trigger diseases or cause undesirable genetic alterations (Elhafi et al., 2004). Efficient decontamination of surfaces to kill or eliminate active biomolecules would therefore represent an additional safety gain in all areas of water quality and hygiene.

In practice, there is consequently a need for improved materials, methods, and processes for the efficient and particularly also non-toxic and non-corrosive complete decontamination and disinfection of water or aqueous solution to kill or eliminate microorganisms and active biomolecules such as for example DNA, RNA, and proteins.

SUMMARY OF THE INVENTION

The object of the present invention is therefore to overcome the disadvantages of prior art and develop novel materials and methods that achieve improved and expanded action of silver technology.

According to the invention, this object is solved by a silver- and ruthenium-containing surface of the bioactive device that additionally comprises at least one vitamin or at least one derivative of a vitamin, at least one surface-active substance and/or at least one divalent or trivalent metal ion.

According to the invention, the object is further solved by a bioactive coating comprising at least ruthenium and additionally at least one vitamin or at least one derivative of a vitamin, at least one surface-active substance and/or at least one divalent or trivalent metal ion. Advantageously, the coating according to the invention can comprise either additionally silver or, instead of ruthenium, silver-ruthenium bimetallic particles, or it can also be applied to a silver-containing surface of a device or another article.

The function of the ruthenium molecules on the silver surface or in direct contact with silver molecules is to allow for a quicker release of silver ions, but they also simultaneously function as "anchor points" for bonding and complexing vitamins or derivatives thereof, i.e. for example ascorbic acid molecules or derivatives thereof.

In addition, the object is solved by a method for producing a bioactive device, in particular by providing a device having a silver- and ruthenium-containing surface, or applying a ruthenium coating to a silver-containing surface of the device, or applying a silver coating to the device and subsequently applying a ruthenium coating to the silver coating, or applying ruthenium-silver particles to the device; and applying at least one vitamin or at least one derivative of a vitamin, at least one surface-active substance and/or at least one divalent or trivalent metal ion to the surface comprising silver and ruthenium of the device.

The object is further solved by a method for coating a device, in particular by applying a ruthenium coating to a silver-containing surface of the device, or applying a silver coating to the device and subsequently applying a ruthenium coating to the silver coating, or applying ruthenium-silver particles to the device; and applying at least one vitamin or at least one derivative of a vitamin, at least one surface-active substance and/or at least one divalent or trivalent metal ion to the silver and ruthenium comprising surface of the device.

In the invention present here, the oligodynamic effect of silver for reducing the amount of germs known per se is significantly improved and increased by combining silver with ruthenium and a vitamin, preferably ascorbic acid or derivatives thereof. These novel bioactive metal surfaces lead to faster and more efficient killing of microorganisms. Simultaneously, these novel metal surfaces prevent infestation by microorganisms and attachment or permanent deposition of biomolecules such as DNA, RNA, or proteins. A self-cleaning surface is thus obtained, which very quickly and efficiently and over extended periods of time sterilizes water or aqueous solutions when they come in contact with said surface.

The silver-containing surface or silver surface to be co-used according to the invention can be the surface of an appropriate compact or solid material. In principle however, the device according to the invention can also comprise any other material (such as for example plastic material, ceramics, glass, etc.) having an applied thin, silver-containing coating, which together with the applied outer ruthenium coating forms an effective ruthenium-silver sandwich system having a silver or silver alloy bottom layer or base and a humidity- or moisture-permeable ruthenium outer layer, top layer, or covering layer.

The coatings or coating systems according to the invention, i.e. the ruthenium coating and an optionally required silver bottom layer (generally of a thickness of 2-10 μm) are preferably applied or deposited galvanically. Other coating methods, such as PVD, CVD, sputtering, sol, gel, and reduction methods, are also plating methods suitable for this purpose.

Here, the application of ruthenium coatings is controlled in such a way that the silver-containing surface is in moisture contact with the environment or can get into moisture contact with the environment through continuous, preferably finely formed, free surface areas, openings, pores, cracks, spacings or the like in the ruthenium coating, and moisture contact between silver and ruthenium is thereby guaranteed. If the silver surface is occupied by ruthenium clusters, the oligodynamic effect of silver can be increased in an advantageous manner. The ruthenium layers, which are preferably cluster-like, porous or contain microcracks, in combination with silver allow for a much more efficient release of silver ions to the environment. Preferably, ruthenium is applied in a thickness in the nanometer or micrometer range, a thickness of a maximum of about 2 μm, in particular about 0.05 μm, and a minimum of about 0.005-0.01 μm being particularly useful.

However, Ag—Ru particles wherein silver and ruthenium are in electrically conductive contact and moisture or water is wetting both metals can also be used. The silver-ruthenium bimetallic particles can be present in the micrometer or nanometer range, preferably in the nanometer range with a size of approximately <50 nm. Silver and ruthenium particles can also be effective as individual particles if close metallic contact between both particle types exists.

Nanometer- and micrometer-sized metal particles can be produced for example by milling, electrochemical, electroless, capillary electrophoresis, hydrothermal synthesis, PVD, CVD, or sol-gel methods. Nanoparticle of ruthenium-silver (Wu et al., 1990 II), platinum-ruthenium (Schmidt et al., 1998), ruthenium-copper (Wu et al., 1990 I), and ruthenium-gold (Wu et al., 1990 II) are preferably produced for catalytic purposes in prior art.

Electrodeposition, in particular the deposition of the preferably cluster-like, porous or microcrack-containing ruthenium layers according to the invention, can be selectively controlled by selecting a suitable electrolyte, by the metal content in the electrolyte, the electrolyte temperature, the pH of the electrolyte, the duration of the deposition or processing time and/or by means of the current density or amount of current. Hence, the structure and dimensions of the ruthenium clusters, (micro-)pores and microcracks in the ruthenium layer according to the invention in particular are determined by the selected electrodeposition conditions, so that the thickness and structure of the ruthenium layer can be adjusted or devised according to the requirements and tailored to the respective application. In the electrodeposition, not only a simple and known conventional process conduct, where the individual layers of a ruthenium-silver sandwich system according to the invention can simply be deposited consecutively, can be utilized, but electrolyte systems that are commercially available, known, and proven can also used for this purpose.

Prior to coating, the surfaces are preferably first cleaned and subjected to pickling and/or rinsing. In case of a non-conductive device, the surface of the device has to be pre-treated in accordance with methods known to electroplating specialists prior to application of a silver and ruthenium coating to allow for a peel-resistant coating with silver and ruthenium.

A first indication of the special synergistic interaction between ruthenium and ascorbic acid provided the finding that ruthenium can be used very efficiently in novel decontamination solutions with vitamin derivatives, metal ions, and detergents.

Novel solutions and methods with divalent or trivalent metal ions, vitamin derivatives, and detergents were developed that overcome the disadvantages of prior art for universal disinfecting and decontaminating solutions and do not use aggressive, corrosive chemicals or strongly oxidizing agents and in addition completely decontaminate the treated substrates at room temperature or slightly elevated temperatures.

It is known that in physiological quantities of micromolar concentrations, antioxidants in combination with divalent metal ions can sporadically lead to damage to and partial strand breaks in nucleic acid molecules (Padayatty et al., 2003; Blokhina et al., 2003; Veal et al., 1991). However, these are only sporadic, isolated results that are only applicable to each particular case.

Systematic testing of novel combinations of metal ions, vitamin derivatives, and detergents resulted in the development of highly efficient, universal, novel decontaminating and disinfecting solutions. Further, most recent tests prove that ruthenium also has a highly efficient synergistic effect in this system (see FIG. 1).

Surprisingly, it was then newly found in addition, however, that incubating newly-developed metal surfaces coated with silver and ruthenium in ascorbic acid solutions results in spontaneous bonding and complexing of the ascorbic acid molecules to the ruthenium molecules. A sustained depot of ascorbic acid molecules is thereby formed on the metal surface. An adjoining silver and ruthenium coating is also possible as long as metallic contact exists. A porous, microcracks-containing silver layer on top of a porous ruthenium layer is also conceivable provided there is contact between both metals through an aqueous solution. These newly developed coating systems of silver, ruthenium, and ascorbic acid and/or divalent and/or trivalent metal ions of the fourth period and/or subgroups I, II, and VIII of the periodic table and/or inert surfactants have totally new, surprising properties.

The new properties of these metal surfaces lead to much faster and more efficient killing of microorganisms as is possible with the existing materials and methods of prior art.

Comparison of different silver samples with silver/ruthenium coatings after ascorbic acid treatment with respect to germicidal efficiency makes this obvious.

Round silver sheets having a diameter of 1.3 cm were galvanically provided with the respective microporous coatings and then incubated for 24 hours in 0.5 M aqueous ascorbic acid solution. After incubation, the sheets were washed twice with sterilized water. A silver/ruthenium sheet (Ag/Ru) treated with ascorbic acid in this manner kills germs much faster than reference samples. For example, bacteria of a test culture were already drastically reduced in bacterial count after 2 to 20 minutes or even killed completely (see FIG. 2A to 2D). After treatment with ascorbic acid, the different reference samples having a pure silver sheet (Ag), silver sheet with gold coating (Ag/Au), or silver sheet with palladium and nickel coating (Ag/Pd/Ni) show the first significant reduction of the bacterial count only after about 60 minutes of contact or exposure time without achieving complete destruction of all germs in this period of time.

Multiple washing with sterilized water of the silver-ruthenium surfaces treated with ascorbic acid also does not significantly reduce the increased antibacterial action (see FIGS. 3A to 3D). This shows that the ascorbic acid molecules have experienced strong bonding on the surface of silver and ruthenium and form a depot. Furthermore, a special synergistic interaction exists between all three components.

When necessary, the ascorbic acid depot can be replenished by simple application of or even merely wiping with an aqueous ascorbic acid solution. Alternatively, replenishing of the depot can also occur by means of reincubation in an ascorbic acid solution.

Supplementing the ascorbic acid depot by applying a thin layer of ascorbic acid, metal ions, and detergents has the special additional effect that nucleic acid molecules are now also quickly and completely degraded when they come in contact with this surface. A crucial new point for sustained depot formation is hereby the cluster-like, porous or microcracks-containing ruthenium-silver layers preferred according to the invention that support efficient depot formation.

A disadvantage of prior art for silver technology but also for most bioactive surfaces in general is a missing degradation function for problematic biomolecules such as DNA, RNA, or proteins. Our own investigations prove that different plastic or metal surfaces have no or only a very limited degrading effect on DNA molecules (see FIG. 4).

The special synergistic effect of the novel Ag/Ru coatings in combination with ascorbic acid, metal ions, and detergents becomes apparent in studies about the stability of DNA molecules on surfaces coated in this manner. If defined DNA samples are applied to these surfaces as contamination, analysis by agarose gel and electrophoresis shows fast, complete degradation within 30 minutes to 24 hours. Further analyses using the highly sensitive PCR technology show that after just 30 minutes, the applied DNA molecules are no longer detectable (see FIG. 6). A reference sample on a plastic surface shows no DNA degradation in this period of time. Hence, the novel bioactive surfaces have the additional property of a self-cleaning surface for problematic biomolecules.

A further subject matter of the present invention is the use of the bioactive devices, coatings, and metal surfaces according to the invention for making and keeping water or aqueous solutions free of germs to safeguard hygiene and water quality.

Further advantageous embodiments of the present invention are revealed by the subject matters of the subordinate claims.

The efficient action of the novel metal surfaces is all the more surprising since it has been proven that each of the individual components does not show a comparable efficient action.

Only when the metal surfaces or coatings of silver and ruthenium are loaded with at least one vitamin or derivatives thereof and preferably also with additional divalent or trivalent metal ions and/or detergents, a synergistic effect and a faster, more efficient sterilization of aqueous solutions and the degradation of problematic biomolecules on these metal surfaces or coatings results.

The metal surfaces or coatings to be produced according to the invention therefore comprise silver, ruthenium, and preferably ascorbic acid or derivatives thereof.

The vitamin or salts or acidic derivatives thereof preferably to be co-used according to the invention are one or more compounds and/or salts thereof selected from the group of water-soluble vitamins having the properties of antioxidants, such as preferably vitamin C, riboflavin, and niacin. It is co-used in quantities of about 1 mM to 1000 mM based on the total solution, preferably in quantities of about 10 mM to 100 mM.

An additional increase of the action can be achieved by applying thin layers of ascorbic acid or derivatives thereof and additional surface-active substances. The surface-active substances to be co-used according to the invention are anionic, non-ionic, amphoteric, or cationic inert surfactants or suitable mixtures with each other or among one another. In particular, alkyl ether sulfates, alkyl and/or aryl sulfonates, alkyl sulfates, amphosurfactants, betaines, alkylamidoalkylamines, alkyl-substituted amino acids, alkyl-substituted imino acids, acylated amino acids, and amphosurfactant combinations can be used. In principle, all inert surfactants are suitable. Inert means that they affect neither the synergistic solution nor the test result. Anionic and non-ionic surfactants are preferred according to the invention.

They are used in quantities of about 0.1 to 10% by weight based on the total solution, preferably in quantities of about 0.2 to 0.5% by weight.

Divalent and/or trivalent metal ions can be applied additionally to the bioactive surfaces according to the invention. These are ions of metals of the fourth period and/or subgroups I, II, and VIII of the periodic table of the elements. They are used in the form of salts thereof with organic and/or inorganic acids or bases. One or more compounds selected from subgroup VIII, in particular iron, cobalt, nickel, copper, or zinc, are preferred according to the invention.

They are used in quantities of about 1 mM to 100 mM based on the total solution, preferably in quantities of about mM to 10 mM.

In addition, further common inert auxiliary agents and additives such as for example suitable buffer substances for adjusting a defined pH, such as Tris tris(hydroxymethyl) aminomethane, MES (2-(morpholino) ethanesulfonic acid), HEPES (2-[4-(2-hydroxyethyl)-1-piperazinyl]ethanesulfonic acid), MOPS (3-(N-morpholino)propanesulfonic acid), carbonates and derivatives of succinic acid, can be applied to the bioactive surfaces according to the invention. These buffer substances are used in quantities of about 1 mM to 500 mM based on the total solution.

As contact or exposure time between bioactive metal surfaces according to the invention and water or aqueous solutions, about 5 to 20 minutes at room temperature or slightly elevated temperature are generally sufficient for complete decontamination and disinfection. However, the applied methods may be varied and can be adapted to the respective requirements.

The present invention allows the development of novel bioactive surfaces for hygiene applications and the production of high quality water by means of coatings of silver, ruthenium, and ascorbic acid or derivatives thereof. With that, a new leap in the quality of the decontamination and disinfection by silver technology is achieved since a faster antimicrobial action in combination with sustained long-term protection is hereby possible. At the same time, permanent attachment of active biomolecules, such as DNA, RNA, or proteins, to the surface is prevented. The invention is illustrated by means of the following exemplary figures and exemplary embodiments.

BRIEF DESCRIPTION OF THE FIGURES

FIGS. 2A-D show the increased antimicrobial action of the coatings of silver, ruthenium, and ascorbic acid according to the invention in comparison with other silver samples of prior art.

FIGS. 3A-D show the same test as in FIG. 2 after the metal sheets identical to those from FIG. 2 have been washed again with sterilized water and dried.

EXAMPLES AND DESCRIPTION OF DIFFERENT AND PREFERRED EMBODIMENTS OF THE INVENTION

Figure 1:
FIG. 1 shows the special synergistic effect between ruthenium and ascorbic acid using the example of the degradation of DNA molecules.

FIG. 1 shows the special synergistic effect between ruthenium and ascorbic acid using the example of the degradation of DNA molecules. Identical aliquots of DNA plasmids (YEp351) were treated for 2 minutes with the solutions for samples 1-7 listed below. Subsequently, the DNA samples were denatured and the single-stranded DNA molecules separated by gel electrophoresis on a agarose gel (1%). After staining with ethidium bromide, the presented pictures are obtained. The control shows the intact plasmid DNA after treatment with sterilized water. With the introduction of strand breaks, the molecular weight of the affected DNA molecules is reduced. This can be determined in the gel by a comparison with the control and the molecular weight marker. In each case, 5 µg of DNA in 5 µl of sterile Tris buffer (1 mmM; pH 8.0) war treated for 2 minutes at room temperature with 5 µl of the solutions for samples 1-7 listed below. Subsequently, the samples were mixed with 5 µl of 100 mM Tris (pH 12), bromophenol blue marker was added to the mixture, and the samples were denatured for 5 minutes at 95° C. The denatured samples were immediately cooled to 4° C. and aliquots of 1 µg of DNA each per lane were applied. After gel electrophoresis in 1% agarose gel, the DNA was stained with ethidium bromide and photographed.

Sample Information:

M: DNA marker 1 kb ladder; K: control: DNA+5 µl of sterilized $H_2O$; 1: 100 mM ascorbic acid+10 mM $FeCl_3$; 2: 100 mM ascorbic acid+10 mM $FeCl_3$; 3: 100 mM ascorbic acid+10 mM $RuCl_3$; 4: 100 mM ascorbic acid+1 mM $RuCl_3$; 5: 100 mM ascorbic acid+10 mM $AgNO_3$; 6: 10 mM benzoic acid; 7: 100 mM ascorbic acid FIGS. 2A-D show the increased antimicrobial action of the novel coatings of silver, ruthenium, and ascorbic acid in comparison with other silver samples. The metal sheets (1.3 cm in diameter) were incubated in 0.5 M ascorbic acid solution, then washed with sterilized water, and dried. After drying, the samples were added to 1 ml of sterilized water each containing $10^5$ bacteria of standard strain *Escherichia coli* RRI. The number of living bacteria was determined after 1, 5, 20, and 60 minutes and is given from $10^5$ to $10^0$.

Samples: 0: sterilized $H_2O$ only; 1: pure silver sheet (Ag); 2: silver sheet with ruthenium (Ag/Ru); 3: silver sheet with gold (Ag/Au); 4: silver sheet with palladium and nickel (Ag/Pd/Ni); 5: 100 mM ascorbic acid, 10 mM $FeCl_3$; 6: 100 mM ascorbic acid, 10 mM $RuCl_3$, (5+6 each with 0.3% SDS and 0.2% Tween 20).

FIGS. 3A-D show the same test as in FIG. 2 after the metal sheets identical to those from FIG. 2 have been washed again with sterilized water and dried. After drying, the samples were again added to 1 ml of sterilized water each containing $10^5$ bacteria of standard strain *Escherichia coli* RRI. The number of living bacteria was determined after 1, 5, 20, and 60 minutes and is given from $10^5$ to $10^0$.

Samples: 0: sterilized $H_2O$ only; 1: pure silver sheet (Ag); 2: silver sheet with ruthenium (Ag/Ru); 3: silver sheet with gold (Ag/Au); 4: silver sheet with palladium and nickel (Ag/Pd/Ni); 5: 100 mM ascorbic acid, 10 mM $FeCl_3$; 6: 100 mM ascorbic acid, 10 mM $RuCl_3$, (5+6 each with 0.3% SDS and 0.2% Tween 20).

Figure 4:
FIG. 4 shows an analysis of the stability of DNA molecules on different surfaces.

FIG. 4 shows an analysis of the stability of DNA molecules on different surfaces. In each case, 50 µl of a DNA solution (25 ng/µl) were added dropwise to the surfaces. Aliquots of 2 µl each were removed after 24 hours and examined in analytical agarose gel. After gel electrophoresis in 1% agarose gel, the DNA was stained with ethidium bromide and photographed. Sterile plastic material was used as control surface.

Gel Application:

K: control sample from plastic surface

M: marker/1 kb ladder

1: DNA sample from Ag after ascorbic acid treatment

2: DNA sample from Ag/Au after ascorbic acid treatment

3: DNA sample from Ag/Ru after ascorbic acid treatment

4: DNA sample from Pd/Ni after ascorbic acid treatment

Figure 5:
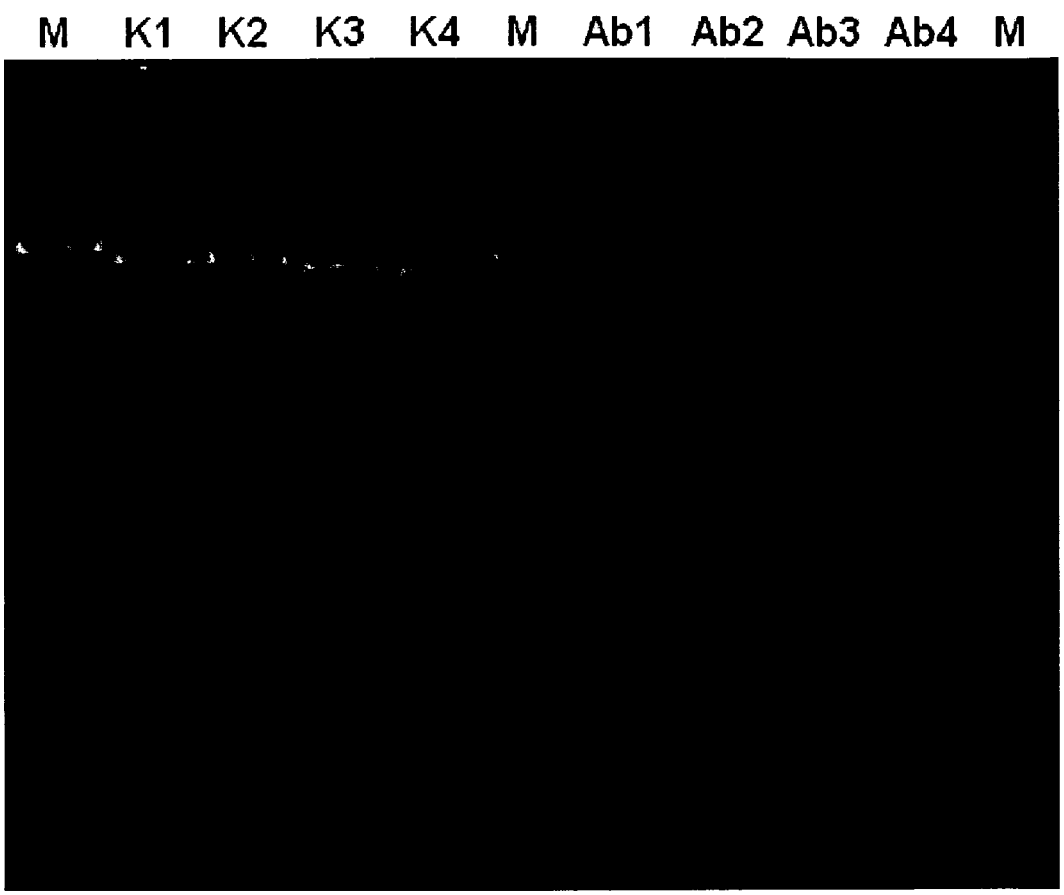
FIG. 5 shows an analysis of the efficient DNA degradation on the novel metal surfaces having a special coating.

FIG. 5 shows an analysis of the efficient DNA degradation on the novel metal surfaces having a special coating. The Ag/Ru coating was additionally provided with a thin layer of ascorbic acid, metal ions, and detergents. For this, a solution with 100 mM ascorbic acid, 10 mM $FeCl_3$, 0.3% SDS, and 0.2% Tween 20 was applied to the surface by quick immersion, allowing the excess to drip off, and drying. Subsequently, 50 µl of a DNA solution (25 ng/µl) was added dropwise to the surfaces. Aliquots of 2 µl each were removed after the specified times and the DNA was stained with ethidium bromide after gel electrophoresis in 1% agarose gel and photographed. Sterile plastic material was used as control surface.

Figure 6:
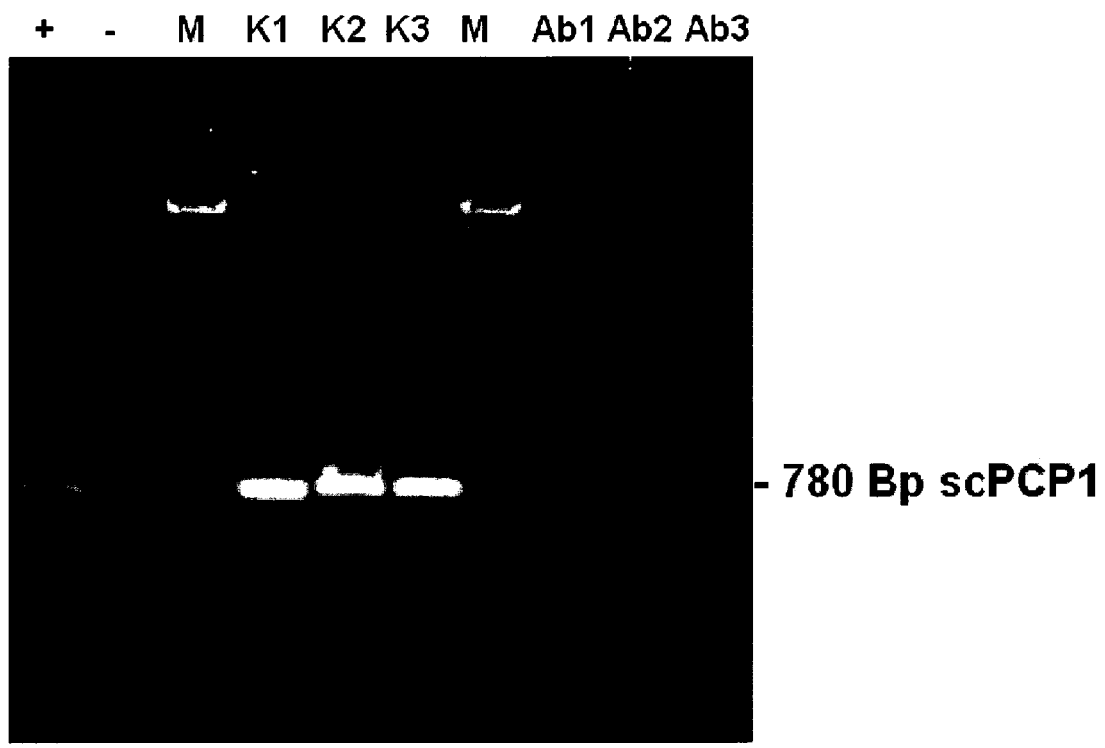
FIG. 6 shows a PCR analysis of DNA samples after different contact times with the novel metal surfaces coated according to the invention.

Gel application:
M: marker/1 kb ladder
K1: control sample from the plastic surface after 30 minutes
K2: control sample from the plastic surface after 1 hour
K3: control sample from the plastic surface after 4 hours
K4: control sample from the plastic surface after 24 hours
Ab1: DNA sample from the coated surface after 30 minutes
Ab2: DNA sample from the coated surface after 1 hour
Ab3: DNA sample from the coated surface after 4 hours
Ab4: DNA sample from the coated surface after 24 hours FIG. 6 shows a PCR analysis of DNA samples after different contact times with the coated novel metal surfaces. The Ag/Ru coatings were additionally provided with a thin layer of ascorbic acid, metal ions, and detergents. For this, a solution with 100 mM ascorbic acid, 10 mM $FeCl_3$, 0.3% SDS, and 0.2% Tween 20 was applied to the surface by quick immersion, allowing the excess to drip off, and drying. Subsequently, 50 μl of a DNA solution (0.1 ng/μl) was added dropwise to the surfaces. Aliquots of 2 μl each were removed after the specified times and each transferred into a 50 μl PCR reaction mix with a pipette. The PCR reaction mix contains primer pairs for the amplification of the test DNA (scPCP1 gene of yeast). The controls (+/−) indicate if the PCR reaction was successful. A band of 780 base pairs (bp) of the test DNA indicates that intact DNA molecules are still present for this gene. If the test DNA has been completely eliminated or destroyed, no amplified DNA bands are detectable in the gel.

After gel electrophoresis in 1% agarose gel, the DNA was stained with ethidium bromide and photographed. Sterile plastic material was used as control surface.

Gel Application:
+: positive control of the PCR reaction with test DNA
−: negative control of the PCR reaction without DNA
M: marker/1 kb ladder
K1: control sample from the plastic surface after 30 minutes
K2: control sample from the plastic surface after 1 hour
K3: control sample from the plastic surface after 4 hours
Ab1: DNA sample from the coated surface after 30 minutes
Ab2: DNA sample from the coated surface after 1 hour
Ab3: DNA sample from the coated surface after 4 hours

LIST OF EXPLANATIONS FOR THE ABBREVIATIONS IN THE FIGURES

Ag: argentum/silver
Ag): pure silver sheet
Ag/Ru): silver sheet with ruthenium coating
Ag/Au): silver sheet with gold coating
Ag/Pd/Ni): silver sheet with palladium and nickel coating
EtBr: ethidium bromide
K: control
M: molecular weight marker
PCR: polymerase chain reaction
RT: room temperature
Ru: ruthenium
sc: *Saccharomyces cerevisiae*
scPCP1: *Saccharomyces cerevisiae* gene for processing of cytochrome c peroxidase
SDS: sodium dodecyl sulfate
YEp351: yeast episomal plasmid

LITERATURE

Blokhina O., Virolainen E., Fagerstedt K. V. (2003): Antioxidants, Oxidative Damage and Oxygen Deprivation Stress: A Review. Annals Botany 91:179-194

Elhafi, G., Naylor, C. J., Savage, C. E. and Jones, R. C. (2004): Microwave or autoclave treatments destroy the infectivity of infectious bronchitis virus and avian pneumovirus but allow detection by reverse transcriptase-polymerase chain reaction. Avian Pathology 33, 3003-306

Padayatty S. J., Katz A., Wang Y., Eck P., Kwon O., Lee J. H., Chen S., Corpe C., Dutta A., Dutta S. K. and Levine M. (2003): Vitamin C as an antioxidant: evaluation of its role in disease prevention. J. Am. Coll. Nutr. 1, 18-35

Schmidt, T. J., Noeske, M., Gasteiger, H. A., Behm, R. J., Britz, P., Bönnemann, H. (1998): PtRu Alloy Colloids as Precursors for Fuel Cell Catalysts. J. Electrochem. Soc. 145, 925

Veal J. M., Merchant K. & Rill R. L. (1991): The influence of reducing agent and 1,10-phenanthroline concentration on DNA cleavage by phenanthroline+copper. Nucl Acids Res. Vol. 19, No. 12, 3383-3388

Wu, X., Gerstein, B. C., King, T. S. (1990) I: Characterization of Silica-Supported Cu Monometallic and Ru—Cu Bimetallic Catalysts by Hydrogen Chemisorption and NMR of Adsorbed Hydrogen. J. Catal. 121, 271-293

Wu, X., Gerstein, B. C., King, T. S. (1990) II: Characterization of Silica-Supported Ru—Ag and Ru—Au Bimetallic Catalysts by Hydrogen Chemisorption and NMR of Adsorbed Hydrogen. J. of Catalysis 123, 43-49

The invention claimed is:

1. A bioactive device comprising a metallic silver- and a metallic ruthenium-containing surface, wherein ascorbic acid is bound to said surface.

2. The bioactive device according to claim 1, wherein said silver- and ruthenium-containing surface is designed in such a way that silver-ruthenium contacts are in moisture contact with the environment.

3. A bioactive metal coating for a surface, comprising at least metallic ruthenium or silver-ruthenium bimetallic particles and additionally ascorbic acid, wherein said surface is a metallic silver-containing surface coated with said metallic ruthenium or silver-ruthenium bimetallic particles to create a coated surface, and wherein said ascorbic acid is bound to said coated surface.

4. The bioactive coating according to claim 3, wherein said coating additionally comprises silver.

5. The bioactive coating according to claim 3, wherein the ruthenium-containing coating has a thickness in the range of 5 nm to 2 μm.

6. The bioactive coating according to claim 3, wherein the ruthenium-containing coating is cluster-like, microporous and/or contains microcracks.

7. A method for producing a bioactive device according to claim 1 comprising:
  providing a device having a metallic silver- and a metallic ruthenium-containing surface, or
  applying a metallic ruthenium coating to a metallic silver-containing surface of the device, or
  applying a metallic silver coating to the device and subsequently applying a metallic ruthenium coating to the silver coating, or
  applying ruthenium-silver bimetallic particles to the device; and
  applying ascorbic acid to the surface comprising metallic silver and metallic ruthenium.

8. A method for coating a device according to claim 1 comprising:
  applying a metallic ruthenium coating to a metallic silver-containing surface of the device, or applying a metallic silver coating to the device and subsequently applying a metallic ruthenium coating to the silver coating, or applying ruthenium-silver bimetallic particles to the device; and applying ascorbic acid to the surface comprising metallic silver and metallic ruthenium.

9. The method according to claim 7 or 8, wherein the metallic silver coating and/or metallic ruthenium coating is/are designed in such a way that it/they is/are in moisture contact with the environment.

10. The method according to claim 7 or 8 wherein the metallic ruthenium coating is applied in a thickness of 5 nm to 2 µm or in a thickness of 2-10 µm.

11. The method according to claim 7 or 8, wherein a cluster-like, microporous and/or microcracks-containing metallic ruthenium coating is applied.

12. The method according to claim 7 or 8, wherein the metallic ruthenium coating and/or silver coating is/are produced by electrochemical, electroless, PVD, CVD, sputtering, reduction, and sol-gel methods.

13. The method according to claim 7 or 8, wherein that the silver-ruthenium particles are produced as bimetallic particles that are metallically bonded to one another.

14. The method according to claim 13, wherein the bimetallic particles are produced with sizes in the micrometer range, nanometer range, or with a size of <50 nm.

15. The method according to claim 7 or 8, wherein the ruthenium and silver particles are produced as pure metal particles and are brought into close metallic contact to produce the silver-ruthenium particles.

16. The method according to claim 15, wherein the individual metal particles of silver and/or ruthenium are produced with sizes in the micrometer range or nanometer range, or with a size of <50 nm.

17. A method for decontaminating or disinfecting water or aqueous solutions comprising providing the device of claim 1, and decontaminating or disinfecting water or aqueous solutions by contacting the solution with the device.

18. The method of claim 7, wherein the metallic ruthenium and metallic silver is loaded with said ascorbic acid.

19. The bioactive device according to claim 1, wherein the ascorbic acid is bonded to the ruthenium molecules.

20. A bioactive device according to claim 1, wherein the ruthenium-containing surface is cluster-like, microporous and/or contains microcracks.

21. A bioactive device according to claim 20, wherein the ruthenium-containing surface is cluster-like and/or contains microcracks.

22. A bioactive device according to claim 21, wherein the ruthenium-containing surface contains microcracks.

23. The bioactive device according to claim 1, wherein said metal surface comprises a depot of said ascorbic acid bound to said surface.

24. The bioactive coating according to claim 3, wherein said metal coating comprises a depot of said ascorbic acid bound to said surface.

25. The bioactive device according to claim 1, wherein the metallic silver- and metallic ruthenium-comprising surface is composed of a silver or silver alloy layer and a humidity- or moisture-permeable ruthenium layer, wherein silver-ruthenium contacts are in moisture contact with the environment.

26. The bioactive device according to claim 25, wherein the ruthenium-layer is cluster-like, microporous and/or contains microcracks.

27. The bioactive device according to claim 1 further comprising a coating which comprises at least metallic ruthenium or silver-ruthenium bimetallic particles and which is applied to said surface, wherein silver-ruthenium contacts are in moisture contact with the environment.

28. The bioactive device according to claim 27, wherein the ruthenium-containing coating is cluster-like, microporous and/or contains microcracks.

29. The bioactive coating of claim 3, wherein the coating comprises metallic ruthenium, wherein the coated surface is designed in such a way that silver-ruthenium contacts are in moisture contact with the environment.

30. The bioactive device according to claim 29, wherein the ruthenium-containing coating is cluster-like, microporous and/or contains microcracks.

31. The bioactive coating of claim 3, comprising silver-ruthenium bimetallic particles, wherein the coated surface is designed in such a way that silver-ruthenium contacts are in moisture contact with the environment.

32. The bioactive device according to claim 31, wherein the ruthenium-containing coating is cluster-like, microporous and/or contains microcracks.

* * * * *